(12) United States Patent
Felts et al.

(10) Patent No.: US 8,947,653 B1
(45) Date of Patent: Feb. 3, 2015

(54) BOTTLE COATING DETECTION SYSTEM AND METHOD

(75) Inventors: John Thomas Felts, Alameda, CA (US); Christopher John Felts, Alameda, CA (US)

(73) Assignee: Nano Scale Surface Systems, Inc., Alameda, CA (US)

( * ) Notice: Subject to any disclaimer, the term of this patent is extended or adjusted under 35 U.S.C. 154(b) by 146 days.

(21) Appl. No.: 13/471,041

(22) Filed: May 14, 2012

(51) Int. Cl.
*G01N 21/00* (2006.01)
*G01N 21/90* (2006.01)
*G01N 21/954* (2006.01)

(52) U.S. Cl.
CPC .......... *G01N 21/9072* (2013.01); *G01N 21/954* (2013.01); *G01N 21/9054* (2013.01)
USPC ....................................................... 356/240.1

(58) Field of Classification Search
None
See application file for complete search history.

(56) References Cited

U.S. PATENT DOCUMENTS

| | | | |
|---|---|---|---|
| 6,006,001 A * | 12/1999 | Alfano et al. | 385/115 |
| 6,015,595 A | 1/2000 | Felts | |
| 6,112,695 A | 9/2000 | Felts | |
| 6,177,142 B1 | 1/2001 | Felts | |
| 6,180,185 B1 | 1/2001 | Felts | |
| 6,180,191 B1 | 1/2001 | Felts | |
| 6,539,890 B1 | 4/2003 | Felts | |
| 6,961,123 B1 * | 11/2005 | Wang et al. | 356/364 |
| 7,369,240 B1 * | 5/2008 | Abbott et al. | 356/429 |
| 7,480,040 B2 * | 1/2009 | Juvinall et al. | 356/239.4 |
| 7,513,953 B1 | 4/2009 | Felts | |

* cited by examiner

*Primary Examiner* — Kara Geisel
*Assistant Examiner* — Amanda Merlino
(74) *Attorney, Agent, or Firm* — Innovation Counsel LLP; Serge J. Hodgson

(57) ABSTRACT

A method for detecting a coating on a bottle includes directing light at a first point of incidence on the bottle and detecting a first intensity of reflected light from the first point of incidence on the bottle. Further, light is directed at a second point of incidence on the bottle and a second intensity of reflected light from the second point of incidence on the bottle is detected. The first intensity is compared to the second intensity to determine whether the coating on the bottle has been uniformly deposited.

16 Claims, 4 Drawing Sheets

BOTTLE COATING DETECTION SYSTEM AND METHOD

BACKGROUND

1. Field of the Invention

The present invention relates to plastics packaging equipment. More particularly, the present invention relates to bottle coating equipment.

2. Description of the Related Art

One of the greatest challenges in the plastics packaging business has been the reduction of gas transfer through polymeric materials to either stop gases from ingressing into the packaged product, or to stop gases from egressing from the packaged product. There have been many approaches attempted including new resin formulations and multi-layers of polymeric materials, but each has had problems finding widespread acceptance due to either the cost, non-recyclability or the performance.

Traditionally, polyester terephthalate (PET) is the polymer of choice when gas barrier is needed in plastic packaging. In the three-dimensional (or rigid packaging area), PET is used in almost all applications where shelf-life and clarity are required although poly propylene (PP) is also frequently used.

Rigid packaging, sometimes called three-dimensional packaging, includes bottles, cans, cups and typically excludes the so-called flexible packaging. Examples of flexible packaging include pouches, and bags.

Although widely used in rigid packaging, PET and PP are limited in their ability to provide gas barrier to both gas coming into the product (gas ingress) and escaping (gas egress). In the case of beer, a highly oxygen sensitive beverage, even the oxygen that is adsorbed in the wall of the PET/PP bottle can significantly alter the taste and shelf-life of the beer. For carbonated soft drinks (CSD), on the other hand, the barrier must stop carbon dioxide from escaping out of the beverage and there are little to no concerns about the ingress of gases.

One conventional approach to providing barriers in PET/PP bottles is surface coating technologies where a thin layer is applied to the interior and/or exterior surface of the PET/PP bottle. With this approach, thin film coatings are deposited by chemical vapor deposition utilizing plasma enhanced chemical vapor deposition (PECVD), where the coating is derived from gases that are decomposed within the bottle by a plasma.

To insure that the thin film coating provides an adequate barrier, it is important that the thin film coating cover the entire interior and/or exterior surface of the bottle. However, the thin film coating is transparent and thin, typically on the order of 20 to 500 nm. Thus, it is not possible to determine whether the entire interior and/or exterior surface of the bottle has been coated with the thin film coating from a visual observation of the bottle with the naked eye.

SUMMARY

A method for detecting a coating on a bottle includes directing light at a first point of incidence on the bottle and detecting a first intensity of reflected light from the first point of incidence on the bottle. Further, light is directed at a second point of incidence on the bottle and a second intensity of reflected light from the second point of incidence on the bottle is detected. The first intensity is compared to the second intensity to determine whether the coating on the bottle has been uniformly deposited.

In this manner, the uniformity of a deposited coating is characterized. Otherwise, the deposited coating is not visibly observable with the naked eye.

Embodiments are best understood by reference to the following detailed description when read in conjunction with the accompanying drawings.

BRIEF DESCRIPTION OF THE DRAWINGS

Common reference numerals are used throughout the drawings and detailed description to indicate like elements.

DETAILED DESCRIPTION

As an overview and in accordance with one embodiment, referring to FIGS. 1, 4, 5, and 7 together, a coating 408 is formed on a bottle 102. Undesirably, coating 408 is not uniform, but is formed on a coated region 402 of bottle 102 and is not formed on an uncoated region 404 of bottle 102.

Figure 4:
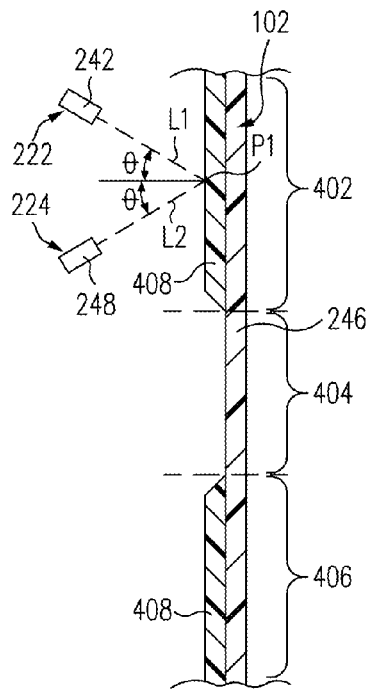
FIGS. 4, 5, 6 are enlarged cross sectional views of the bottle coating detection system of FIGS. 1-2 measuring a coating at different positions along a bottle in accordance with one embodiment.

To characterize the uniformity of coating 408, light is directed at a first point P1 of incidence on coated region 402 of bottle 102 as illustrated in FIG. 4. A first intensity α of reflected light from first point P1 of incidence on coated region 402 of bottle 102 is measured as shown in graph 700 of FIG. 7.

Figure 5:
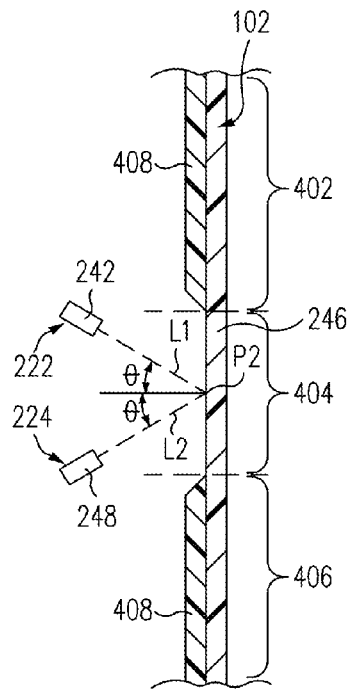

Further, light is directed at a second point P2 of incidence on uncoated region 404 of bottle 102 as illustrated in FIG. 5. A second intensity β of reflected light from second point P2 of incidence on uncoated region 404 of bottle 102 is measured as shown in graph 700 of FIG. 7. First intensity α is different than second intensity β allowing a determination to be made that coating 408 has not been uniformly deposited on bottle 102.

Figure 1:
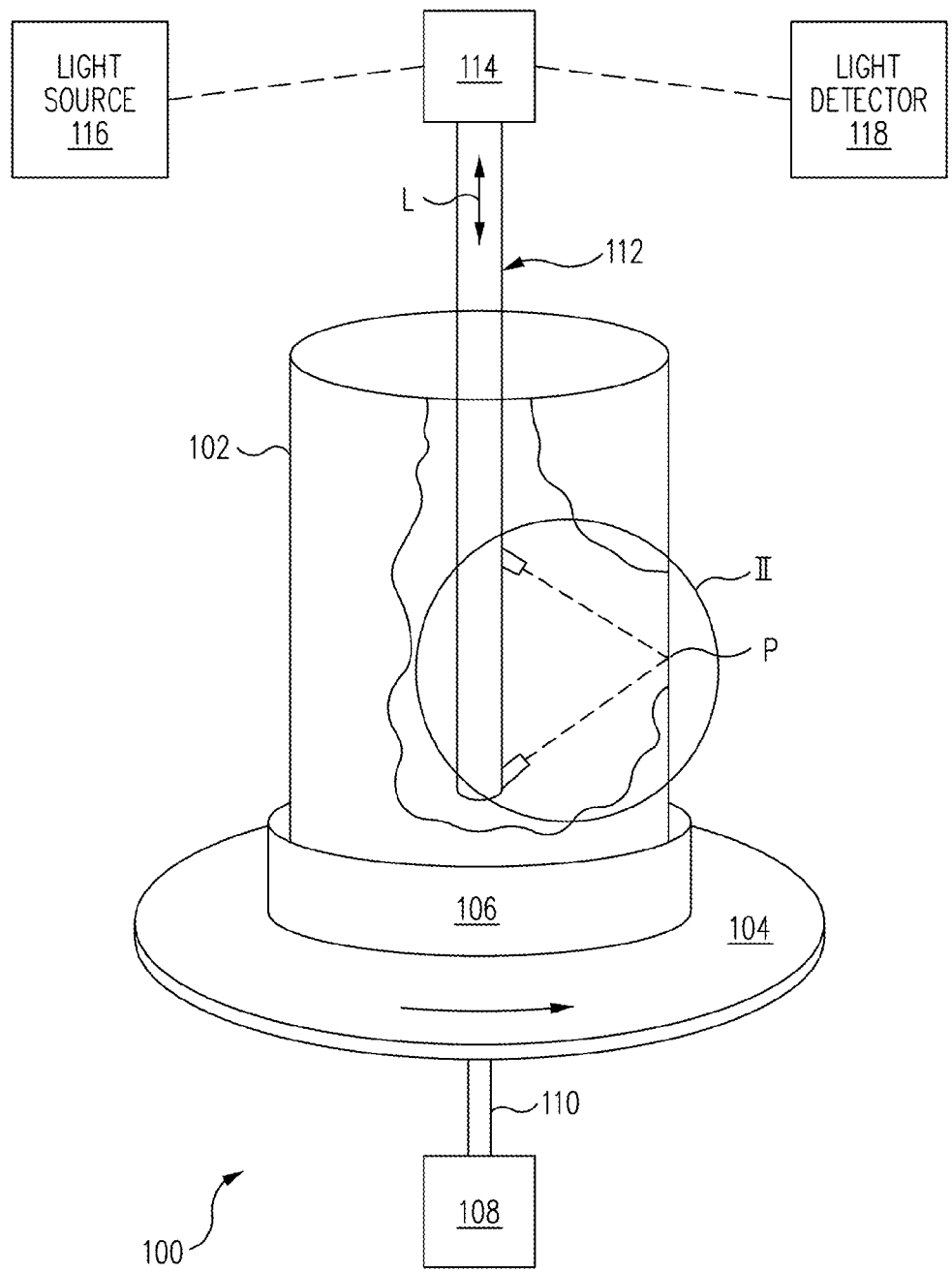
FIG. 1 is a perspective view of a bottle coating detection system for detecting a coating on a bottle in accordance with one embodiment.

Now in more detail, FIG. 1 is a perspective view of a bottle coating detection system 100 for detecting a coating on a bottle 102 in accordance with one embodiment. Bottle coating detection system 100, sometimes called a detection system for detecting a coating on bottle 102, includes a bottle support 104, sometimes called a table or pedestal.

Bottle support 104 supports bottle 102 allowing detection of a coating on bottle 102. Bottle 102 is sometimes called a base polymer substrate. Bottle 102 has a three dimensional shape and is unacceptably permeable to gas and/or other substances. For example, bottle 102 is a sports bottle and absorbs taste from sport drinks and cross-contaminates other sports drinks placed in the sports bottle from the absorbed taste.

Accordingly, a coating has been applied to bottle 102. Bottle coating detection system 100 is used to determine whether this coating has been applied uniformly or not to bottle 102. However, in another embodiment, bottle 102 is characterized as set forth below without a coating being formed thereon.

Bottle support 104 includes a clamp 106 into which bottle 102 is inserted. Although only the bottom portion of bottle 102 is illustrated as being inserted within clamp 106, in other embodiments, most or all of bottle 102 is inserted within clamp 106. Further, although clamp 106 is illustrated, bottle 102 is supported by bottle support 104 using other supporting means in other embodiments.

Bottle coating detection system 100 further includes a bottle support motor 108. Bottle support motor 108 is coupled to bottle support 104 by a bottle support rotation shaft 110. During operation, bottle support motor 108 rotates bottle support rotation shaft 110 to rotate bottle support 104 and bottle 102 mounted thereto.

Figure 2:
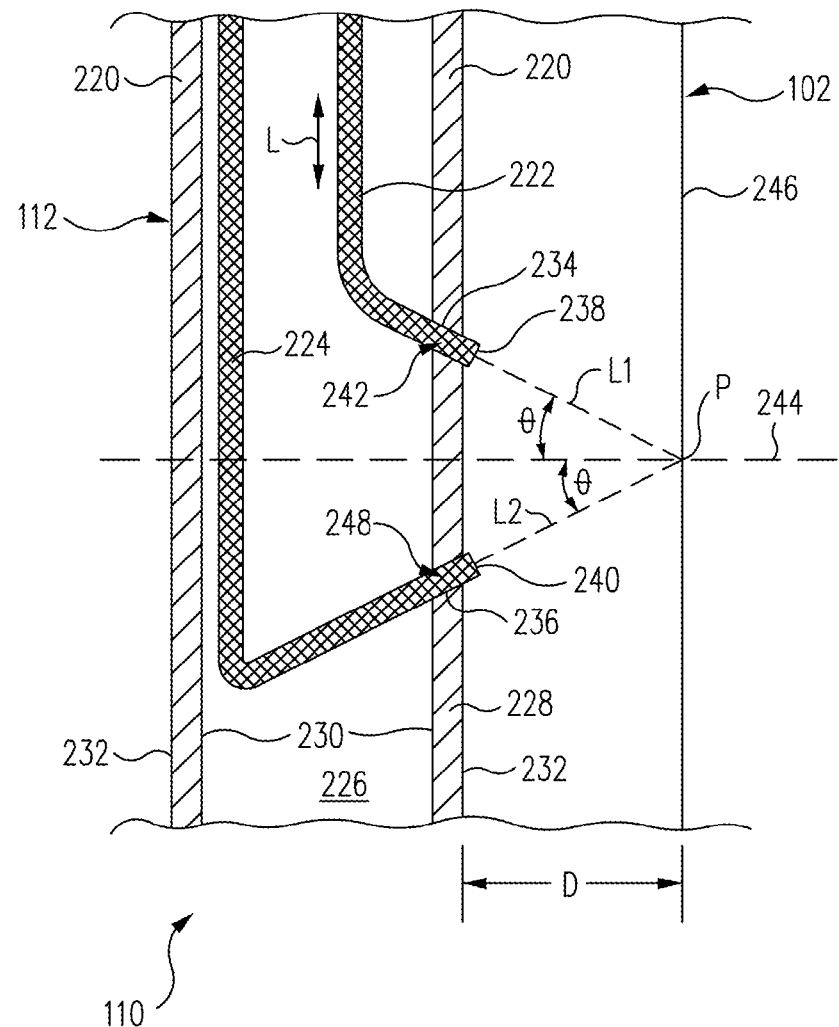
FIG. 2 is an enlarged cross-sectional view of the region II of the bottle coating detection system of FIG. 1 in accordance with one embodiment.

Bottle coating detection system 100 further includes a bottle coating detection probe 112, a probe motor 114, a light source 116, and a light detector 118. FIG. 2 is an enlarged cross-sectional view of the region II of bottle coating detection system 100 of FIG. 1 in accordance with one embodiment.

Referring now to FIGS. 1 and 2 together, bottle coating detection probe 112 is for directing light at a point P of incidence on bottle 102 and for receiving reflected light from point P of incidence on bottle 102 as discussed below. Bottle coating detection probe 112 includes a hollow probe shaft 220, a light transmitting guide 222, and a light receiving guide 224. In accordance with this embodiment, probe shaft 220 is a cylindrical hollow tube having a light guide lumen 226 therein.

Probe shaft 220 includes a cylindrical sidewall 228 having an interior cylindrical surface 230 and exterior cylindrical surface 232. Interior cylindrical surface 230 defines light guide lumen 226.

Probe shaft 220 further includes a light transmitting guide aperture 234 and a light receiving guide aperture 236. Apertures 234, 236 extend entirely through sidewall 228 and between interior cylindrical surface 230 and exterior cylindrical surface 232.

Light transmitting guide 222 is a light guide through which light is transmitted. In one embodiment, light transmitting guide 222 is a fiber optic cable for light transmission as those of skill in the art will understand in light of this disclosure. Light transmitting guide 222 includes a light emitting face 238. Light emitting face 238 is a surface, e.g., a planar circular surface.

Light transmitting guide 222 is coupled to light source 116, e.g., a polarized laser. During operation, light source 116 generates light that is transmitted through light transmitting guide 222 and exits light transmitting guide 222 through light emitting face 238. In one embodiment, the light exits light emitting face 238 along a line L1 normal to the plane of light emitting face 238.

Similarly, light receiving guide 224 is a light guide through which light is transmitted. In one embodiment, light receiving guide 224 is a fiber optic cable for light transmission as those of skill in the art will understand in light of this disclosure. Light receiving guide 224 includes a light receiving face 240. Light receiving face 240 is a surface, e.g., a planar circular surface.

Light receiving guide 224 is coupled to light detector 118. During operation, light detector 118 receives light that enters light receiving face 240 and is transmitted through light receiving guide 224 to light detector 118. In one embodiment, the light enters light receiving face 240 along a line L2 normal to the plane of light receiving face 240.

A tip 242 of light transmitting guide 222 is mounted within light transmitting guide aperture 234. Tip 242 includes a portion of light transmitting guide 222 adjacent light emitting face 238.

Tip 242 is mounted within light transmitting guide aperture 234 at an angle θ with respect to a plane 244 perpendicular (normal) to a longitudinal axis L of probe shaft 220. More particularly, tip 242 is mounted within light transmitting guide aperture 234 at an angle θ with respect to plane 244 perpendicular to a wall 246 of bottle 102.

Wall 246 is measured as set forth below to determine whether or not a coating is present on wall 246. The angle θ is sometimes called the angle of incidence and is the angle between a ray from tip 242 incident on wall 246 and the line perpendicular to wall 246 at the point P of incidence, sometimes called normal.

Angle θ is within the range of 50 degrees to 89 degrees in one embodiment. In one embodiment, angle θ is determined empirically. For example, the angle is adjusted until the maximum reflected light intensity from bottle 102 when uncoated is received. This angle of maximum reflected light is then selected as angle θ.

In one embodiment, light transmitting guide aperture 234 is drilled at angle θ with respect to plane 244. The diameter of light transmitting guide aperture 234 is slightly larger than tip 242 allowing tip 242 to be slipped into light transmitting guide aperture 234 and thus held at angle θ. However, in other embodiments, tip 242 is glued, clamped, or otherwise held within light transmitting guide aperture 234 at angle θ.

Similarly, a tip 248 of light receiving guide 224 is mounted within light receiving guide aperture 236. Tip 248 includes a portion of light receiving guide 224 adjacent light receiving face 240.

Tip 248 is mounted within light receiving guide aperture 236 at an angle θ with respect to plane 244. The angle θ is sometimes called the angle of incidence and is the angle between a ray from tip 248 incident on wall 246 and the line perpendicular to wall 246 at the point P of incidence, sometimes called normal.

In one embodiment, light receiving guide aperture 236 is drilled at angle θ with respect to plane 244. The diameter of light receiving guide aperture 236 is slightly larger than tip 248 allowing tip 248 to be slipped into light receiving guide aperture 236 and thus held at angle θ. However, in other embodiments, tip 248 is glued, clamped, or otherwise held within light receiving guide aperture 236 at angle θ.

Light emitting face 238 and light receiving face 240 are generally located directly above one another. In various embodiments, light emitting face 238 and light receiving face 240 are both equally flush with, protrude from, or are recessed from, exterior cylindrical surface 232 of probe shaft 220. Generally, light emitting face 238 and light receiving face 240 are located equidistant from bottle 102 in planes perpendicular to longitudinal axis L of probe shaft 220.

Plane 244 is located equidistant between light emitting face 238 and light receiving face 240. Accordingly, lines L1, L2 intersect plane 244 at a point P of incidence at a distance D from probe shaft 220.

Wall 246 of bottle 102 is located at point P of incidence. In light of this disclosure, by knowing the angle θ and the distance between light emitting face 238 and light receiving face 240, the point P of incidence and distance D is readily calculated using conventional mathematical relationships.

Thus, during use, polarized or other light emitted from light emitting face 238 travels along line L1, is reflected from wall 246 of bottle 102 at point P of incidence, travels along line L2, and enters light receiving face 240. Bottle 102 is placed at point P of incidence so that there is maximum detection of the polarized light when bottle 102 is measured without a coating thereon.

As discussed below in reference to FIGS. 4-5, the magnitude of the light received at light receiving face 240 is indicative of whether or not a coating is present on wall 246.

Generally, light source 116 is for emitting light at point P of incidence on bottle 102 and light detector 118 is for receiving reflected light from point P of incidence on bottle 102.

Figure 3:
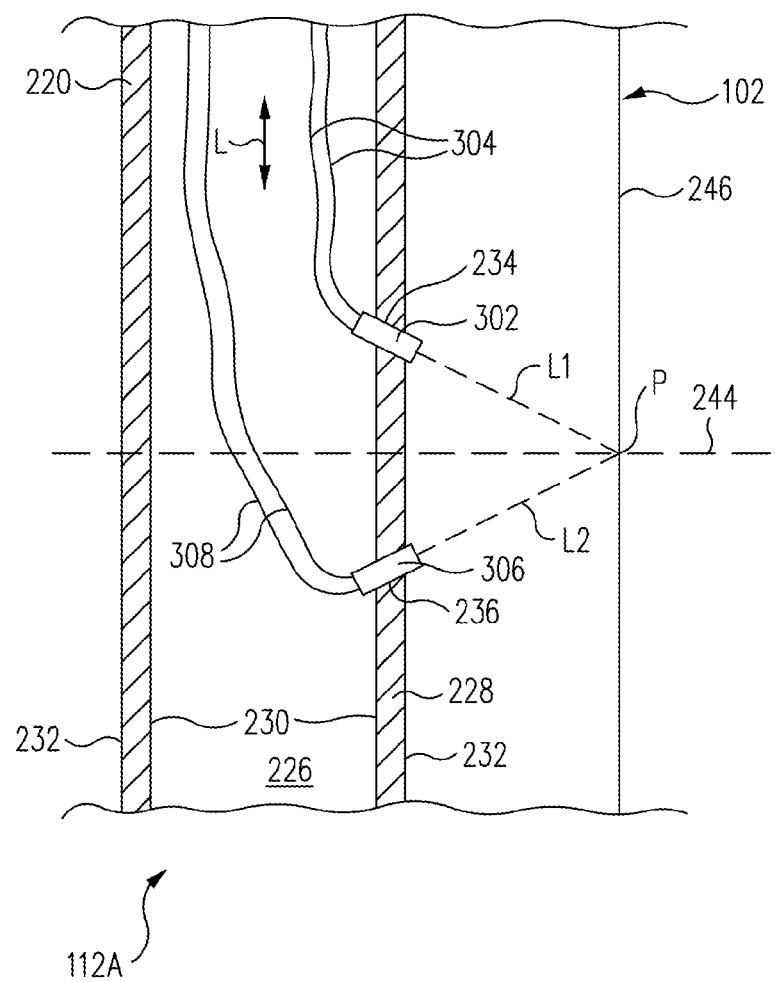
FIG. 3 is an enlarged cross-sectional view of a region of a bottle coating detection probe in accordance with another embodiment.

FIG. 3 is an enlarged cross-sectional view of a region of a bottle coating detection probe 112A in accordance with another embodiment. Bottle coating detection probe 112A of FIG. 3 is similar to bottle coating detection probe 112 of FIG. 2 and only the significant differences are discussed below.

In accordance with this embodiment, a light source 302, e.g., a microlaser, is mounted within light transmitting guide aperture 234. Light source 302 has one or more leads 304 extending through light guide lumen 226. During use, voltage or another signal is provided to light source 302 through leads 304 to cause light source 302 to provide light along line L1.

Similarly, a light detector 306, e.g., a microphotodetector, is mounted within light receiving guide aperture 236. Light detector 306 has one or more leads 308 extending through light guide lumen 226. During use, voltage or another signal is output from light detector 306 through leads 308 depending upon the intensity of the light along line L2 received by light detector 306.

Generally, light source 302 is for emitting light at point P of incidence on bottle 102 and light detector 306 is for receiving reflected light from point P of incidence on bottle 102.

Referring to FIGS. 1, 2, and 3 together, in other embodiments, light source 116 and light transmitting guide 222 are used in conjunction with light detector 306. Alternatively, light source 302 is used in conjunction with light detector 118 and light receiving guide 224.

Figure 6:
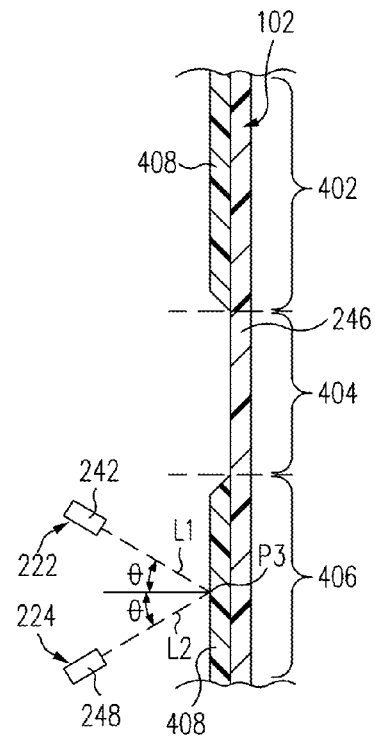
Figure 7:
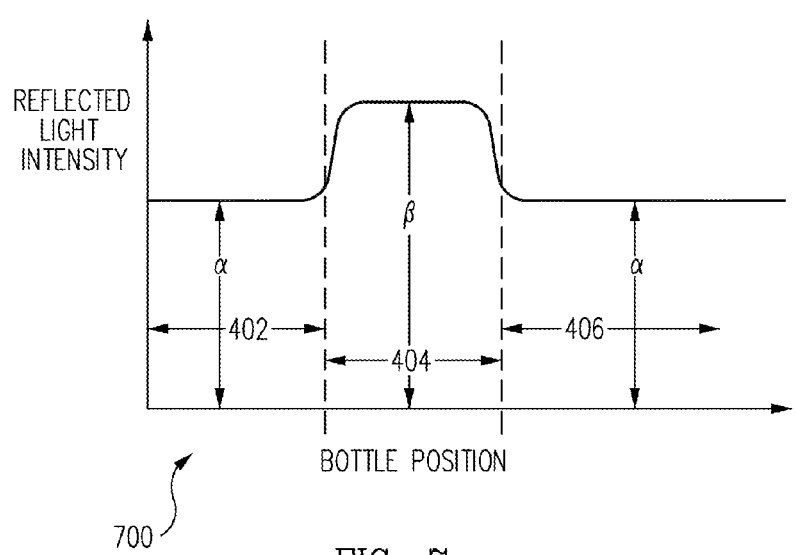
FIG. 7 is a graph of reflected light intensity versus bottle position in accordance with one embodiment.

FIGS. 4, 5, 6 are enlarged cross sectional views of bottle coating detection system 100 of FIGS. 1-2 measuring a coating at different positions along a bottle 102 in accordance with one embodiment. FIG. 7 is a graph 700 of reflected light intensity versus bottle position in accordance with one embodiment.

Referring now to FIGS. 4, 5, 6, and 7 together, bottle 102 is shown extremely enlarged to illustrate coated regions 402, 406 of bottle 102 and an uncoated region 404 of bottle 102. Coated regions 402, 406 contain a coating 408 thereon. Uncoated region 404 is uncoated, i.e., does not have a coating formed thereon.

FIGS. 4, 5, and 6 illustrate an example of a bottle 102 that has not been uniformly coated with coating 408. Such a non-uniform coating 408 is generally undesirable as gas or other substances can pass in and/or out through uncoated region 404 thus degrading or destroying the product to be contained within bottle 102. Coating 408, sometimes called a barrier coating, is substantially impenetrable to the gas or other substance.

In FIGS. 4, 5, 6, only tips 242, 248 are illustrated for simplicity. Tips 242, 248 are illustrated at three different positions in FIGS. 4, 5, 6 representing measurements of coating 408 (or absence thereof) at three different times.

Coating 408 has a first index of refraction different than a second index of refraction of bottle 102. If the index of refraction of coating 408 is less than the index of refraction of bottle 102, the reflection from coating 408, i.e., coating regions 402, 406 will be less than the reflection from uncoated bottle 102, i.e., uncoated region 404. Conversely, if the index of refraction of coating 408 is greater than the index of refraction of bottle 102, the reflection from coating 408, i.e., coating regions 402, 406 will be greater than the reflection from uncoated bottle 102, i.e., uncoated region 404.

In accordance with this illustration, it is assumed the case where the index of refraction of coating 408 is less than the index of refraction of bottle 102. Accordingly, the reflection from coating 408, i.e., coating regions 402, 406 is less than the reflection from uncoated bottle 102, i.e., uncoated region 404.

In graph 700, the X or horizontal axis represents position along bottle 102 at regions 402, 404, 406 and the Y or vertical axis represents reflected light intensity as received by light receiving guide 224.

Paying particular attention now to FIGS. 4, 6, and 7 together, in coated regions 402, 406, i.e., at first points P1, P3 of incidence, the reflected light intensity as received by light receiving guide 224 is measured as having a first value $\alpha$.

Paying particular attention now to FIGS. 5 and 7 together, in uncoated region 404, i.e., at a second point P2 of incidence, the reflected light intensity as received by light receiving guide 224 is measured as having a second value $\beta$. Second value $\beta$ is greater than first value $\alpha$.

Thus, as graph 700 illustrates, by measuring the reflected light along various positions of bottle 102, a determination is made as to whether bottle 102 is uniformly coated with coating 408. More particularly, in this example, the reflected light intensity $\alpha$ at first points P1, P3 of incidence within coated regions 402, 406 is equal allowing a determination to be made that these regions 402, 406 are uniformly coated with coating 408. Conversely, the reflected light intensity $\beta$ at second point P2 of incidence within uncoated region 404 is different than the reflected light intensity $\alpha$ at first points P1, P3 of incidence within coated regions 402, 406 allowing a determination to be made that these regions 402, 404, 406 are not uniformly coated with coating 408.

Generally, if bottle 102 is uniformly coated with coating 408, the measured reflected light intensity will be uniform across (at various positions) bottle 102. Conversely, if bottle 102 is not uniformly, i.e., un-uniformly, coated with coating 408, the measured reflected light intensity will vary across (at various positions) bottle 102 as illustrated by the example of FIG. 7.

Referring now just to FIG. 1, to fully characterize bottle 102, in one embodiment, bottle support motor 108 spins bottle support 104 at a fixed rate so that bottle coating detection probe 112 is left stationary for one (1) full revolution of bottle 102. Accordingly, the reflected light intensity will be measured around the entire inner circumference of bottle 102 at a particular vertical height of bottle 102.

Once a full revolution of bottle 102 is completed, bottle coating detection probe 112 is moved vertically with respect to bottle 102, e.g., by probe motor 114. This process is repeated in a step wise fashion until the entire bottle 102 is characterized as to whether a coating 408 is present thereon or not.

Probe motor 114 is set forth for moving bottle coating detection probe 112 vertically up and down. This up and down motion of bottle coating detection probe 112 is sometimes called linear motion of bottle coating detection probe 112 as the motion is in line with longitudinal axis L of bottle coating detection probe 112.

In other embodiments, bottle coating detection probe 112 is moved with respect to bottle 102 by moving bottle 102 while holding bottle coating detection probe 112 stationary. For example, bottle support motor 108 drops and raises bottle support 104 and thus bottle 102 while bottle coating detection probe 112 is held stationary.

In one example, low density polyethylene (LDPE) sports bottles with and without a 20 nm silicon dioxide coating were characterized. The coating was deposited from plasma enhanced chemical vapor deposition (PECVD) using hexamethyldisiloxane and oxygen gases in a plasma at approximately 100 mTorr total pressure and an applied power of 200 watts (13.56 MHz).

The bottles were then cut so that a piece of the side wall was removed and the coated and uncoated samples were mounted into an apparatus similar to the one shown in FIGS. 1 and 2 and the resulting reflection measured. The intensity of the reflected light as the angle $\theta$ was varied is set forth below in table 1.

TABLE 1

| Angle $\theta$ | Uncoated sample (Counts) | Coated sample (Counts) | Difference between uncoated and coated sample (Counts) |
|---|---|---|---|
| 40 | 2000 | 1100 | 900 |
| 50 | 2500 | 1500 | 1000 |
| 60 | 2800 | 1700 | 1100 |
| 65 | 3000 | 1800 | 1200 |
| 70 | 3500 | 2200 | 1300 |

This disclosure provides exemplary embodiments of the present invention. The scope of the present invention is not limited by these exemplary embodiments. Numerous variations, whether explicitly provided for by the specification or implied by the specification or not, may be implemented by one of skill in the art in view of this disclosure.

What is claimed is:

1. A detection system comprising:
   a probe shaft comprising:
      a cylindrical sidewall comprising:
         an interior cylindrical surface; and
         an exterior cylindrical surface; and
      a light transmitting guide aperture extending between the interior cylindrical surface and the exterior cylindrical surface at a non-perpendicular angle with respect to a longitudinal axis of the probe shaft;
   a light source for emitting light at the angle at a point of incidence on a substrate;
   a light detector for receiving reflected light from the point of incidence on the substrate, the detection system for detecting a coating on the substrate; and
   a light transmitting guide coupled to the light source, wherein a tip of the light transmitting guide is mounted within the light transmitting guide aperture at the angle, a light emitting face of the light transmitting guide protruding from the exterior cylindrical surface.

2. The detection system of claim 1 wherein the light transmitting guide comprises a fiber optic cable.

3. The detection system of claim 1 wherein the light emitting face is for emitting the light.

4. The detection system of claim 3 wherein the light transmitting guide is mounted to the probe shaft.

5. The detection system of claim 1 further comprising:
   a lumen within the probe shaft, wherein the light detector is mounted to the probe shaft, leads of the light detector extending through the lumen of the probe shaft.

6. The detection system of claim 1 further comprising:
   a light receiving guide coupled to the light detector.

7. The detection system of claim 6 wherein the light receiving guide comprises a fiber optic cable.

8. The detection system of claim 6 wherein the light receiving guide comprises a light receiving face for receiving the light.

9. The detection system of claim 6 wherein the light receiving guide is mounted to the probe shaft.

10. The detection system of claim 9 wherein a tip of the light receiving guide is mounted to the probe shaft at the angle.

11. A detection system for detecting a coating on a substrate comprising:
    a detection probe for directing light at a point of incidence on the substrate and for receiving reflected light from the point of incidence on the substrate, the detection probe comprising:
       a probe shaft comprising:
          a cylindrical sidewall comprising:
             an interior cylindrical surface; and
             an exterior cylindrical surface; and
          a light transmitting guide aperture extending between the interior cylindrical surface and the exterior cylindrical surface at a non-perpendicular angle with respect to a longitudinal axis of the probe shaft; and
       a light transmitting guide, wherein a tip of the light transmitting guide is mounted within the light transmitting guide aperture at the angle, a light emitting face of the light transmitting guide protruding from the exterior cylindrical surface;
    a probe motor for linearly moving the detection probe;
    a bottle support for support the substrate; and
    a bottle support rotation motor for rotating the bottle support.

12. The detection system of claim 11 further comprising:
    a light source for generating the light coupled to the detection probe; and
    a light detector for detecting the reflected light coupled to the detection probe.

13. A method for detecting a coating on a substrate comprising:
    forming a detection probe comprising:
       forming a light transmitting guide aperture in a cylindrical sidewall of a probe shaft, the light transmitting guide aperture extending between an interior cylindrical surface and an exterior cylindrical surface of the cylindrical sidewall at a non-perpendicular angle with respect to a longitudinal axis of the probe shaft; and
       inserting a tip of a light transmitting guide within the light transmitting guide aperture at the angle, a light emitting face of the light transmitting guide protruding from the exterior cylindrical surface;
    directing light from the detection probe at a first point of incidence on the substrate;
    detecting a first intensity of reflected light from the first point of incidence on the substrate with the detection probe;
    linearly moving the detection probe;
    directing light from the detection probe at a second point of incidence on the substrate;
    detecting a second intensity of reflected light from the second point of incidence on the substrate with the detection probe; and
    comparing the first intensity to the second intensity.

14. The method of claim 13 further comprising determining that the coating is uniform upon a determination that the first intensity is equal to the second intensity.

15. The method of claim 13 further comprising determining that the coating is non-uniform upon a determination that the first intensity is different than the second intensity.

16. The method of claim 13 further comprising:
    directing light at the entire substrate; and
    detecting an intensity of reflected light from the entire substrate.

* * * * *